United States Patent [19]

Suzuki et al.

[11] Patent Number: 5,110,205
[45] Date of Patent: May 5, 1992

[54] APPARATUS FOR DETECTING ALCOHOL CONCENTRATION

[75] Inventors: Hiroyoshi Suzuki; Kenji Ogawa; Toru Yamamoto, all of Himeji, Japan

[73] Assignee: Mitsubishi Denki Kabushiki Kaisha, Tokyo, Japan

[21] Appl. No.: 651,080

[22] Filed: Feb. 6, 1991

[30] Foreign Application Priority Data

Feb. 8, 1990 [JP] Japan .................................. 2-30258
Feb. 8, 1990 [JP] Japan .................................. 2-30259

[51] Int. Cl.$^5$ .......................................... G01N 21/41
[52] U.S. Cl. .......................................... 356/135
[58] Field of Search .................................. 350/128–137

[56] References Cited

U.S. PATENT DOCUMENTS

| | | | |
|---|---|---|---|
| 3,426,211 | 2/1969 | Anerson | 356/135 |
| 3,917,410 | 11/1975 | Ulrich . | |
| 3,917,411 | 11/1975 | Schweizer et al. . | |
| 3,977,790 | 8/1976 | Schweizer et al. | 356/136 |
| 4,320,291 | 3/1982 | Uramoto | 356/136 |
| 4,640,615 | 2/1987 | Sasaki | 356/130 |
| 4,641,965 | 2/1987 | Harmer . | |
| 5,015,091 | 5/1991 | Suzuki et al. | 356/135 |

Primary Examiner—Richard A. Rosenberger
Assistant Examiner—Hoa Pham
Attorney, Agent, or Firm—Sughrue, Mion, Zinn, Macpeak and Seas

[57] ABSTRACT

An alcohol concentration detecting apparatus comprising a transparent body (1,1a,1b,1c,1d) transparent to light and having a refraction surface (9) disposed, when in use, in contact with liquid fuel (12) to define an interface between the transparent body and the fuel, the transparent body (1) defining a light path (7,16) for allowing the light to pass through the refraction surface (9) for refracting the light (7). A light-emitting element (4) is disposed on one end of the light path and emitting a light beam (7,16) along the light path, and a position detector element (8) disposed at the other end of the light path for receiving a refracted light beam refracted at the refraction surface (9) and generating an output indicative of the amount of alcohol contained in the fuel. The sensor also comprises an optical lens (6;13,13a,13b,14,14a,14b) for directing and focusing the light beam (7,16) from the light-emitting element (4) onto the optical position detector element (8). The optical lens may include a collimator lens (13) for converting the light beam into a substantially parallel light beam (16), and a condenser lens (14) for focusing the parallel light beam on the position detector element (8).

7 Claims, 8 Drawing Sheets

$$Vout \propto X = \frac{i2}{i1 + i2} \times L$$

APPARATUS FOR DETECTING ALCOHOL CONCENTRATION

BACKGROUND OF THE INVENTION

This invention relates to an alcohol concentration detecting apparatus and, more particularly, to an apparatus for detecting alcohol concentration in liquid fuel by measuring the refraction ratio of the fuel.

In recent years, a mixture of gasoline and alcohol has been increasingly used as fuel for motor vehicles in order to reduce the petroleum consumption. In order to effectively use such alcohol containing gasoline as automotive fuel, the alcohol concentration within the fuel is detected and an actuator such as a fuel injection valve is controlled to regulate the air-to-fuel ratio, the ignition timing and the like in accordance with the alcohol concentration.

Examples of the alcohol concentration detector of this type are disclosed in Japanese Patent Laid-Open No. 57-51920, Japanese Patent Laid-Open No. 58-129235 and Japanese Patent Publication No. 57-12461.

Figure 11:
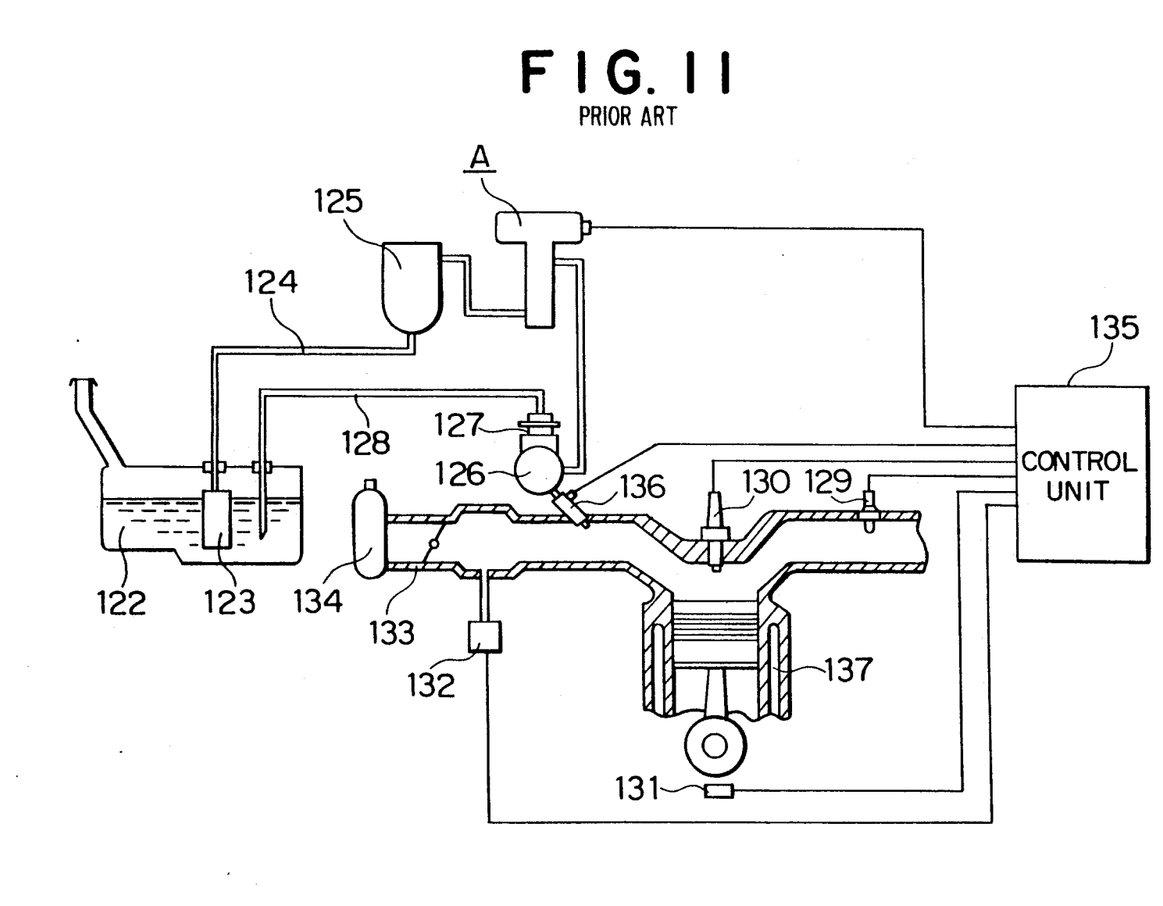
FIG. 11 is a schematic sectional view illustrating an example of an automotive fuel control system employing an alcohol concentration detecting apparatus.

FIG. 11 is a schematic diagram illustrating a fuel control system employing a conventional alcohol concentration detector, in which reference character A indicates an alcohol concentration detector, reference numeral 137 indicates an engine, 136 indicates a fuel injection valve, 122 indicates a fuel tank and 123 indicates a fuel pump.

The fuel within the tank 122 is pumped up by the fuel pump 123 to be fed through a fuel supply pipe 124, a high pressure filter 125, the alcohol concentration detector A, a fuel distributor pipe manifold or pipe 126 to the fuel injection valve 136, where the fuel is injected into the engine 137.

Reference numeral 127 is a fuel pressure regulator 128 is a fuel return pipe, 129 is a air-to-fuel ratio sensor, 130 is an ignition plug, 131 is an engine revolution sensor, 132 is a suction pressure sensor, 133 is a throttle, 134 is an air cleaner and 135 is a control unit.

The control unit 135 receives a signal from the alcohol concentration detector A, a signal from the air-to-fuel ratio sensor and signals from the engine revolution sensor 131 and the suction air pressure sensor 132, in accordance of which the fuel injection valve 136, the ignition plug 130 and the like are driven.

When a fuel to which alcohol is mixed is supplied to the fuel tank 122 and the engine 137 is started, the fuel with alcohol is pumped by the fuel pump 123 to the alcohol concentration detector A, through the fuel pipe 124 and the high pressure filter 125, where the alcohol concentration is measured.

Then the fuel flows into the fuel distribution pipe 126, from where one part of the fuel is supplied to the engine 137 through the fuel injection valve 136 and the other part of the fuel is returned to the fuel tank 122 through the fuel pressure regulator 127 and the fuel return pipe 128.

The fuel pressure regulator always maintains the pressure of the fuel up to the fuel distributor pipe 126 to a constant value.

When the signal indicative of the alcohol content as measured by the alcohol concentration detector A is supplied to the control unit 135, the control unit determines the engine operating state on the basis of the signals from the engine revolution sensor 131, the suction pressure sensor 132 and the like to control the valve open period of the fuel injection valve 136, whereby the fuel amount to be supplied to the engine 137 is changed so that the air-to-fuel ratio varies. The air-to-fuel ratio is detected by the air-to-fuel sensor 129 so that it is feed back-controlled to a target value corresponding to the engine operating state. The control unit also controls the ignition timing of the ignition plug 130 in accordance with the engine operating state.

Figure 12:
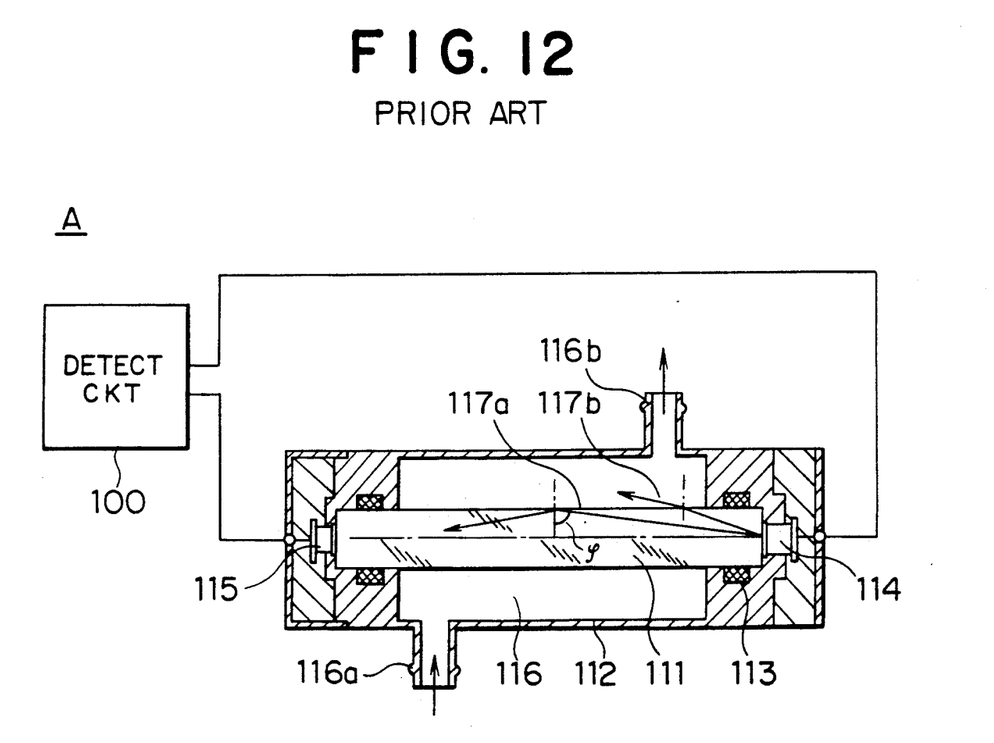
FIG. 12 is an enlarged schematic sectional view illustrating a conventional alcohol concentration detecting apparatus.

FIG. 12 illustrates one example of a conventional alcohol concentration detector A, where reference numeral 111 indicates a cylindrical transparent body, 112 indicates a case, 113 indicates a fuel seal between the cylindrical transparent body and the case, 114 indicates a light-emitting element such as LED, 115 indicates a light-receiving element such as a photo diode, 116 indicates a fuel chamber, 116a indicates a fuel inlet, 116b indicates a fuel outlet, 117a indicates a total reflection light beam, 117b indicates a refraction light beam, and reference numeral 100 indicates a detection circuit for driving the light emitting element 114 and measuring the amount of received light at the light-receiving element 115.

The cylindrical transparent body 111 has a cylindrical circumferential surface in contact with the fuel within the fuel chamber. The light emitted from the light-emitting element 114 impinges at the outer circumference surface of the cylindrical transparent body 111 or at the interface between the transparent body and the fuel. At this time, due to the difference between the refraction index Nf of the fuel and the refraction index Nd of the cylindrical transparent body, a light beam having an angle of incidence equal to or larger than the total reflection angle $\phi = \arcsin(Nf/Nd)$ is totally reflected as indicated as the total reflection light beam 117a to reach the light-receiving element 115, and a light beam having an angle of incidence smaller than the total reflection angle $\phi$ is allowed to enter into the fuel as the refraction light beam 117b. Therefore, the light-receiving element receives only the total reflection light beam 117a which is the light beam having an angle of incidence equal to or larger than the total reflection angle $\phi$.

When the alcohol concentration in the fuel varies, the refraction index Nf of the fuel varies and the angle of total eflection $\phi$ varies accordingly, so that the amount of light that reaches the light-receiving element 5 varies. Then, the alcohol concentration of the fuel can be determined by measuring the output of the light-receiving element.

In the conventional alcohol concentration detecting apparatus constructed as above described, the amount of light emitted from the light-emitting element 114, the sensitivity to light and the peak sensitivity frequency of the light-receiving element 115 are changed in response to the temperature change. Therefore, when the temperature of the alcohol concentration detecting apparatus rises due to the engine heat and the heated fuel, the output of the detecting apparatus varies, so that the alcohol concentration of the fuel cannot precisely be determined.

Also, since the total reflection angle $\phi$ must be relatively large because of the limitation on the refraction index Nd of the cylindrical transparent body, the cylindrical transparent body and therefore the entire alcohol concentration detecting apparatus cannot be made compact.

Further, since the alcohol concentration detecting apparatus must be mounted at a position remote from the engine for the reasons discussed above, it is impossible to immediately, without delay, detect the alcohol concentration of the fuel that is to be injected from the fuel injection valve 136 at the time of starting of the engine, for example.

Particularly, when the engine is to be started immediately after a fuel of a different alcohol concentration has been refilled, there may be a mode of starting operation in which the fuel within the fuel distribution pipe 126 has a different alcohol concentration as compared to that of the fuel within the fuel chamber 116 of the alcohol concentration detector A. In the worst case, it is possible that the engine cannot be started.

SUMMARY OF THE INVENTION

Accordingly, one object of the present invention is to provide an alcohol concentration detecting apparatus that does not greatly depend upon the temperature change.

Another object of the present invention is to provide an alcohol concentration detecting apparatus that can be installed relatively close to the engine.

Another object of the present invention is to provide an alcohol concentration detecting apparatus that can accurately detect the alcohol concentration.

With the above objects in view, the alcohol concentration detecting apparatus of the present invention comprises a transparent body having a refraction surface disposed, when in use, in contact with liquid fuel to define an interface between the transparent body and the fuel. The transparent body defines a light path for allowing the light to pass through the refraction surface for refracting the light emitted from a light-emitting element disposed on one end of the light path and emitting a light beam along the light path. At the other end of the light path, a position detector element is disposed for receiving a refracted light beam refracted at the refraction surface and generating an output indicative of the amount of alcohol contained in the fuel.

In a preferred embodiment of the present invention, a collimator lens and a condenser lens for collimating and focusing the light beam on the position detector element is provided to obtain linear output characteristics. The light path may include first and second light-path sections extending through the transparent body and a third light-path section between the first and second light-path sections extending through the fuel. The light path may include a reflection surface.

BRIEF DESCRIPTION OF THE DRAWINGS

The present invention will become more readily apparent from the following detailed description of the preferred embodiments of the present invention taken in conjunction with the accompanying drawings, in which.

DESCRIPTION OF THE PREFERRED EMBODIMENTS

Figure 1:
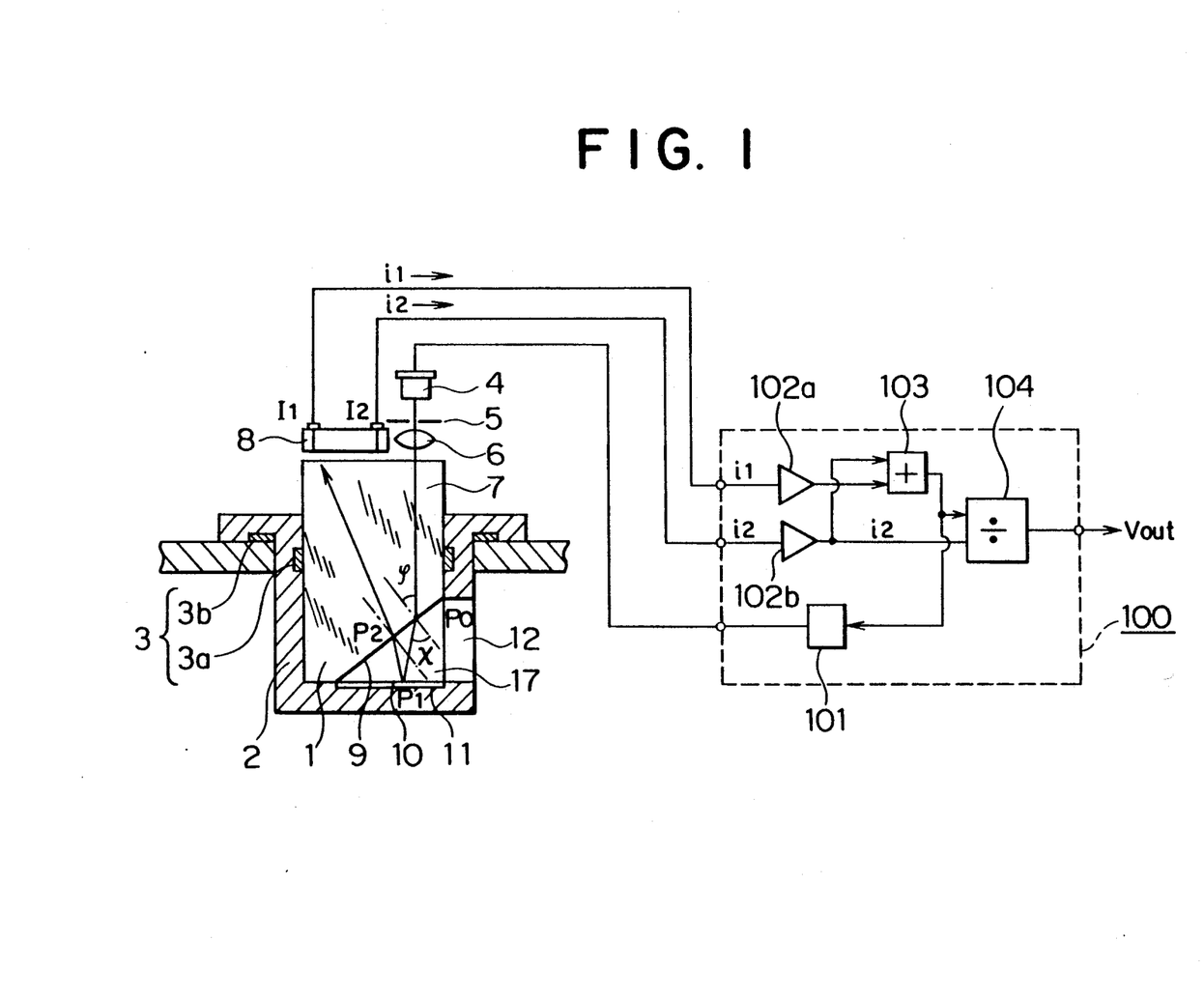
FIG. 1 is a schematic sectional view illustrating an alcohol concentration detecting apparatus of one embodiment of the present invention.

FIG. 1 illustrates one embodiment of the alcohol concentration detecting apparatus of the present invention pertains, in which reference numeral 1 indicates a cylindrical transparent body, 2 indicates a case, and reference numeral 3 indicates a seal unit including a first seal 3a for sealing between the cylindrical transparent body 1 and the case 2 against the ingress of fuel and a second seal 3b for sealing between the case 2 and a fuel passage 12 against the ingress of fuel.

Reference numeral 4 indicates a light-emitting element, 5 indicates a diaphragm, 6 indicates a collecting lens, 7 indicates a collecting light beam, and 8 indicates a one dimensional optical position detector element such as a semiconductor position detector. Reference numeral 9 indicates a refraction surface of the cylindrical transparent body 1 sloped at a predetermined angle with respect to the central axis of the cylindrical transparent body 1 and brought into contact with the fuel introduced through the fuel passage 12. Reference numeral 10 indicates a reflection mirror having a reflection surface 11 on a back side remote from the fuel. The refraction surface 9 and the reflecting mirror 10 together define therebetween a substantially wedge-shaped cavity 17 for receiving the fuel therein.

Reference numeral 100 indicates a detection circuit, which comprises a drive unit 101 for driving the light-emitting element 4, first and second pre-amplifiers 102a and 102b for amplifying a photo-current from the optical position detector 8, an adder 103 for adding the outputs from the first and second pre-amplifiers 102a and 102b and a divider 104 for dividing the output from the second pre-amplifier 102b by the output from the adder 103. The output from the adder 103 is fed back to the drive unit 101.

Figure 2:
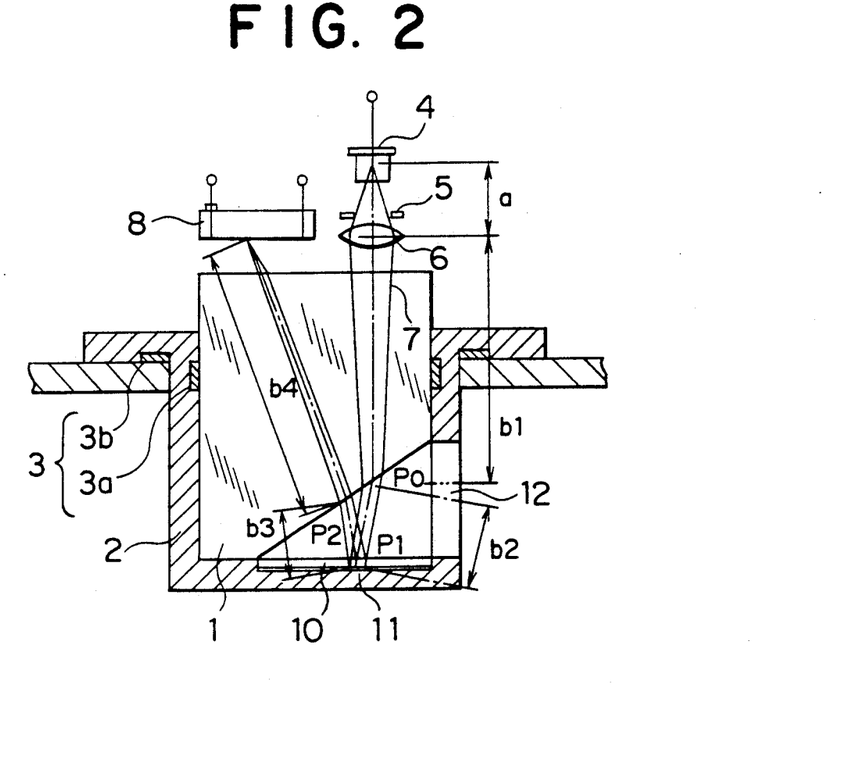
FIG. 2 is a schematic enlarged sectional view illustrating the alcohol concentration detector illustrated.

FIG. 2 illustrates details of the alcohol concentration detector illustrated in FIG. 1, showing only those components indicated by reference numerals 1 to 12 in FIG. 1. Also, FIG. 3 is a diagram for explaining the operation and output characteristics of the optical position detector 8 shown in FIGS. 1 and 2.

The operation of the conventional alcohol concentration detector will now be described. In FIG. 1, when the drive unit 101 drives the light-emitting element 4 disposed on one end of the cylindrical transparent body 1 to emit light, the emitted light passes through the diaphragm 5 and is collected by the collecting lens 6 into the light beam 7 which impinges at the refraction surface 9 on the other end of the cylindrical transparent body 1 at a position Po and at an incident angle of $\phi$.

Figure 3:
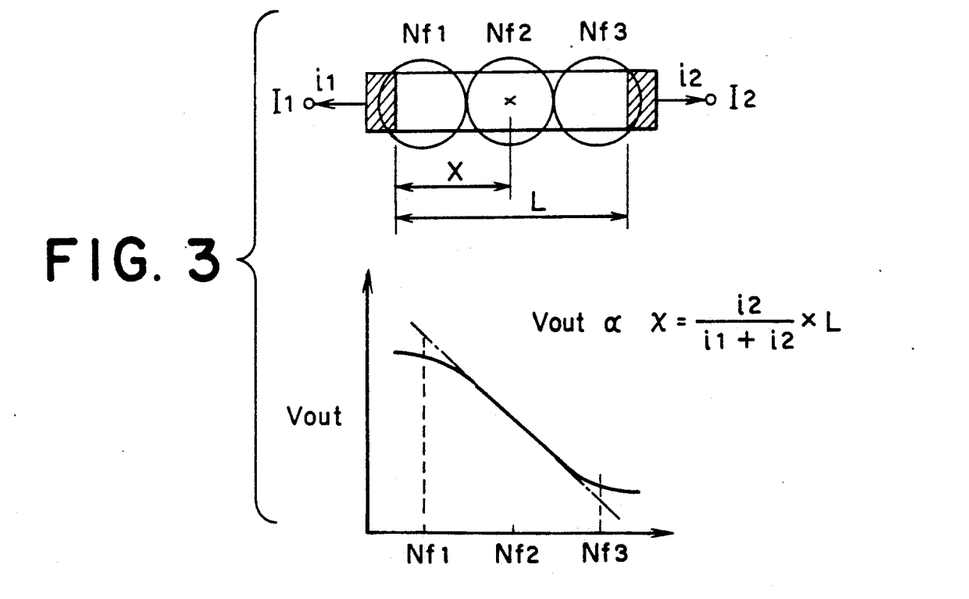
FIG. 3 is a view explaining the principles of the semiconductor position detector.

The refraction surface 9 is in contact with the fuel introduced into a wedge-shaped cavity defined between the sloped refraction surface 9 of the cylindrical transparent body 1 and the case 2 from the fuel passage 12, so that the light beam 7 refracts at the point Po on the refraction surface 9 at a refraction angle $x = \text{arcSIN}(Nd/Nf \times \text{SIN}\phi)$ due to the difference between a refractive index Nf of the fuel shown in FIG. 3 and a refractive index Nd of the cylindrical transparent body 1.

The light beam refracted by the refraction angle x at the point Po travels through the fuel and is reflected at point $P_1$ on the reflecting surface 11 of the reflector 10, and is again refracted at a point $P_2$ on the refraction surface 9 at an angle determined in accordance with the refraction equation between the incident angle $\phi$ and the refraction angle x to pass through the cylindrical transparent body 1. The light beam 7 thus refracted finally reaches the semiconductor optical position detector 8 disposed on the same end as that on which the light-emitting element 4 is disposed. The position detector 8 has a pair of electrodes $I_1$ and $I_2$ from which output currents $i_1$ and $i_2$ are provided.

The lens 6 is selected so that the light beam 7 is focused on the position detector 8. When the light beam 7 impinges at the position detector 8, a photo-current corresponding to the amount of incident light is generated. This current is divided into two currents $i_1$ and $i_2$ at a ratio inverse to the ratio of the distances between the point of light-incidence and the respective electrodes $I_1$ and $I_2$.

In other words, as illustrated in FIG. 3, the distance X between the position on the position detector 8 at which the light impinges and the electrode $I_1$ can be expressed by $X = L \times i_2/(i_1 + i_2)$, where L equals the distance between the two electrodes $I_1$ and $I_2$. The position X coincides with a centroid of the spot of the incident light.

The currents $i_1$ and $i_2$ from the electrodes $I_1$ and $I_2$, respectively, of the semiconductor position detector 8 are supplied to the detector circuit 100, where the supplied currents are amplified by the pre-amplifiers 102a and 102b and added by the adder 103 to provide an output $i_1 + i_2$, by which the output $i_2$ from the preamplifier 102b is divided at the divider 104 to supply an output Vout corresponding to the positional signal x.

At this time, the output from the adder 103 is fed back to the drive unit 101 whereby the drive unit 101 regulates the intensity of the light-emitting element 4 so that the input $(i_1 + i_2)$ is always maintained at a constant.

When the refractive index Nf of the fuel varies as the alcohol concentration of the fuel varies, the refraction index x at the refraction interface 9 varies, so that the incident position X at which the light beam 7 impinges on the semiconductor position detector 8 varies, whereby the output voltage Vout of the detecting circuit 100 is representative of the alcohol concentration of the fuel.

The magnification $\alpha$ of the optical system of the alcohol concentration detecting apparatus can be expressed by $$\alpha = (b_1 + b_2 + b_3 + b_4 + \Delta L(Nd, Nf))/a \quad (1)$$

where, as illustrated in FIG. 2, a is the distance between the light-emitting element 4 and the collecting lens 6, $b_1$ is the distance between the lens 6 and the first refraction point $P_0$, $b_2$ is the distance between the refraction point Po and the reflection point $P_1$, $b_3$ is the distance between the reflection point $P_1$ and the second refraction point $P_2$, $b_4$ is the distance between the refraction point $P_2$ and the semiconductor position detector 8, and $\Delta L(Nd, Nf)$ is a correction term necessary because the light passes through the cylindrical transparent body 1 having the refraction index Nd and the fuel having the refraction index Nf.

In the alcohol concentration detecting apparatus as above described, the distance a cannot be made shorter from the view point of the light beam utilization efficiency, so that the numerator of the equation (1) or the image point distance is made larger by the factor of ten or more than the denominator of the equation (2) or the object point distance. Therefore, the magnification of the optical system of the apparatus is larger than ten, whereby the image of the light-emitting element 4 or the light spot formed on the position detector 8 is relatively large.

According to the alcohol concentration detecting apparatus of the present invention, the output from the apparatus is not greatly affected by temperature change and accurate detection of the alcohol concentration of the fuel is realized. Also, the alcohol concentration detecting apparatus can be installed relatively close to the engine, and this also enables an accurate and immediate detection of the alcohol concentration.

FIG. 3 illustrates the output characteristics of the position detector 8 when the image of the light emitting element 4 on the position detector 8 is large. In this case, when the light spot shifts and a part of the light spot falls off the light-receiving region of the detector 8 as the refraction index Nf of the fuel varies, the centroid of the light spot or the image on the light-receiving region is displaced from the center of the image, making it impossible to detect the true position of the geometrical center of the image. This may cause non-linear output characteristics as seen from the graph illustrated in FIG. 3.

In the alcohol concentration detecting apparatus as above described, since the light-receiving length of the semiconductor position detector element 8 cannot effectively be utilized, the detection range of the refraction index Nf of the fuel is narrow. Also, when the image of the light-spot on the position detector 8 becomes large by the diffusion of the light beam 7 due to the pollution of the refraction surface 9 and the reflection mirror 10, the output characteristics become non-linear.

Further, as understood from equation (1), the magnification $\alpha$ of the optical system of the apparatus is dependent also upon the refraction index Nf of the fuel, the positioning of the position detector element 8 is difficult, so that it is necessary to use a large and expensive semiconductor position detector element 8, making the apparatus large-sized and expensive.

Figure 4:
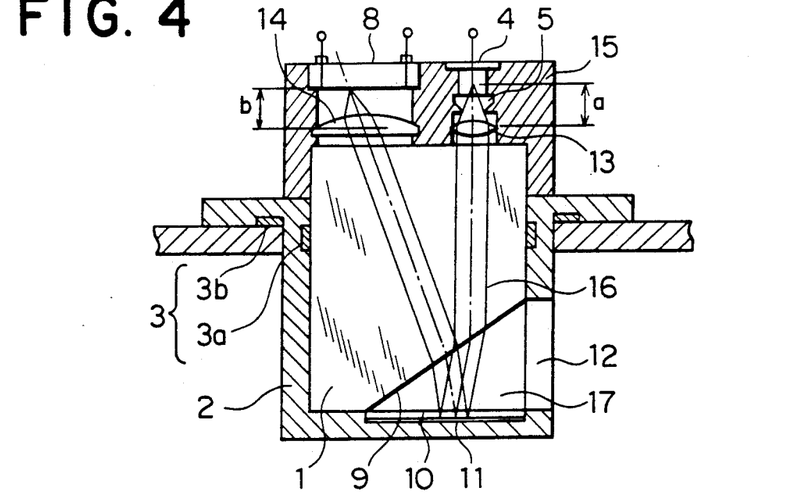
FIG. 4 is a schematic sectional view illustrating another embodiment of the alcohol concentration detecting apparatus of the present invention.

FIG. 4 illustrates another embodiment of the alcohol concentration detecting apparatus of the present invention, in which just above-discussed problems of the alcohol concentration detecting apparatus illustrated and described in conjunction with FIGS. 1 to 3 are eliminated. In FIG. 4, it is seen that the basic structure of the alcohol concentration detecting apparatus is similar, but a collimator lens 13 is mounted between the light-emitting element 4 and the cylindrical transparent body 1 in place of the collecting lens 6 shown in FIG. 1. Therefore, the light beam 16 proceeding into the transparent body 1 is a parallel light beam as distinguished from the collecting light beam 7. Further, a condenser lens 14 is disposed between the cylindrical transparent body 1 and the semiconductor optical position detector 8. A holder 15 is provided for properly supporting the collimator lens 13, the condenser lens 14, the light-emitting element 4, the optical position detector 8 and the like. The holder 15 also has formed therein a diaphragm 5 between the light-emitting element 4 and the collimator lens 13.

While the collimator lens 13 and the condenser lens 14 are illustrated as two separate pieces in FIG. 4, they may be integrally formed in an integrally molded plastic piece having two lens portions corresponding to the lenses 13 and 14, whereby the cost of the detecting apparatus can be reduced.

In the above collimator-condenser optical system, where the magnification $\alpha$ of the optical system is determined by $\alpha = b/a$ where a is the distance between the light-emitting element 4 and the collimator lens 13 (object point distance) and b is the distance between the condenser lens 14 and the optical position detector 8 (image point distance), the magnification $\alpha$ can be made close to 1.

Since the diameter of the light-emitting portion of light-emitting diode commonly used as the light-emitting element 4 is several hundred micro-meters, the diameter of the image of the light spot on the optical position detector in such optical system can be made of the same order, which allows the entire length of the light-receiving region of the optical position detector to be effectively used. Therefore, the alcohol concentration detecting apparatus can be made inexpensive and small-sized and yet have a wide range of detection of the refraction index of the fuel with a small and inexpensive optical position detector having a relatively short light-receiving region.

Further, since the magnification $\alpha$ of the optical system is small, even when the diameter of the image on the optical position detector 8 is increased to a certain extent in the event that the refraction surface 9 of the cylindrical transparent body 1 or the reflecting mirror 10 which are in contact with the fuel in the wedge-shaped cavity 17 are polluted and the parallel light beam 16 is scattered, the linearity of the output characteristics is not adversely affected, providing a reliable, long-life apparatus.

Figure 5:
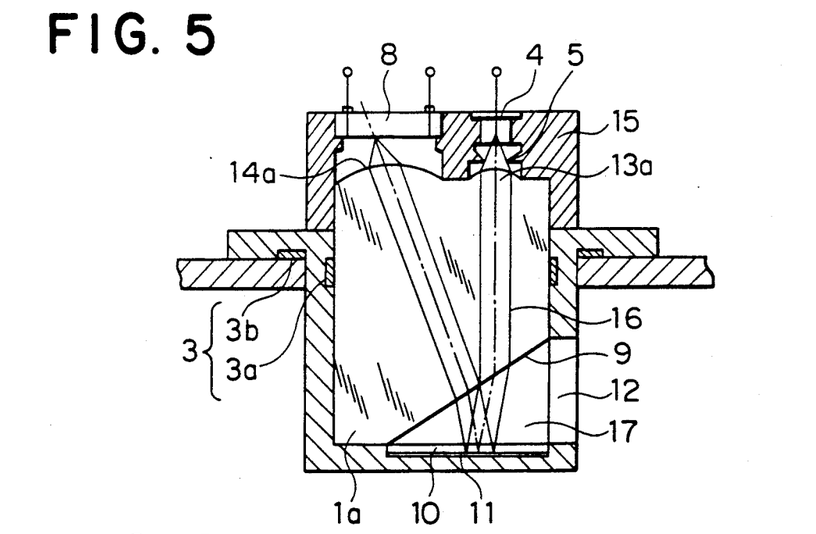
FIG. 5 is a schematic sectional view illustrating a further embodiment of the present invention.

FIG. 5 illustrates another embodiment of the alcohol concentration detection apparatus of the present invention, wherein a cylindrical transparent body 1a has formed on an end face opposite to the refraction surface 9 of the transparent body 1a a collimator lens 13a and a condenser lens 14a which are formed as integral portions of the transparent body 1a. Such transparent body 1a may be formed by any known method. With this structure, undesirable reflections of the light beam at the surfaces of the lenses 13 and 14 and the transparent body 1 are eliminated, so that the optical efficiency of the optical system is much improved. Also, since the number of surfaces subject to pollution is reduced, the operating life from the view point of pollution is increased. Further, the optical system can be manufactured less expensive and compact owing to the combined lens and the transparent body 1a.

Figure 6:
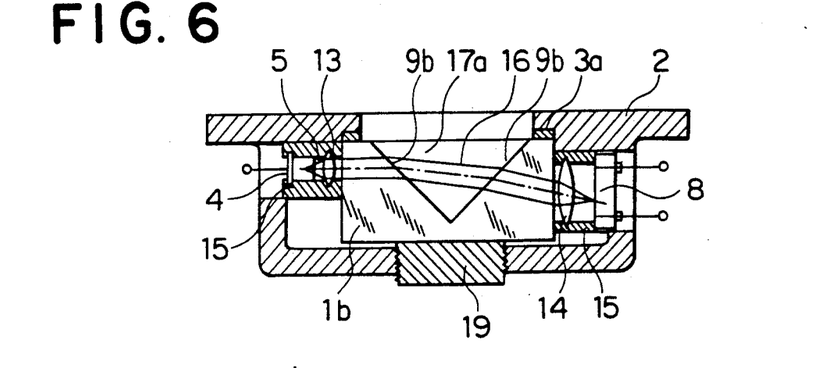
FIG. 6 is a schematic sectional view illustrating another embodiment of the alcohol concentration detecting apparatus of the present invention.

FIG. 6 illustrates another embodiment of the alcohol concentration detecting apparatus of the present invention, which comprises a transparent body 1b having formed a substantially wedge-shaped notch 17a to provide a pair of refraction surfaces 9b which are brought into contact with the fuel. The alcohol concentration detector comprises a light path extending from the light-emitting element 4 to the semiconductor optical position detector 8 through the diaphragm 5, the collimator lens 13, the fist section of the transparent body 1b, the first refraction surface 9b, the wedge-shaped fuel section, the second refraction surface 9b, the second section of the transparent body 1b and the semiconductor position detector 8. It is seen that a holder member 19 is adjustably threaded into the bottom wall of the casing 2 for maintaining the transparent member 1b in intimate sealing relationship with respect to the seal 3a of the casing 2.

The parallel light beam 16 from the collimator lens 13 is refracted at each refraction surface 9b of the transparent body 1b in accordance with the difference in the refraction index between the transparent body 1b and the fuel introduced in the wedge-shaped cavity 17. Then the light beam 16 passes through the condenser lens 14 where the light beam 16 is focused on the semiconductor optical position detector 8. According to the position of the image of the light beam 16 on the light-receiving region of the optical position detector 8, the position detector 8 provides an output signal indicative of the refraction index of the fuel.

According to this embodiment illustrated in FIG. 6, since the reflection mirror 10 used in the previous embodiments is eliminated, the optical efficiency of the optical system is improved, and the operating life from the view point of the pollution of optical system is increased. Also, the optical system can be manufactured less expensively and compactly because the reflection mirror 10 is removed.

While the present invention has been described in terms of several embodiments illustrated in the drawings, many other modifications may be applied. For example, the condenser lens 14 or 14a may be replaced with a non-spherical lens having a cylindrical component which makes the image of the light beam longer in the length direction of the optical position detector 8 than in the width direction of the detector 8. This is advantageous in that the preciseness of the positioning of the optical position detector 8 can be made less severe.

Also, while the semiconductor optical position detector is used as the first optical dimension position detector 8 in the previous embodiments, any suitable position detecting means such as a photo diode array, a one dimensional CCD or the like can equally be utilized instead.

Figure 7:
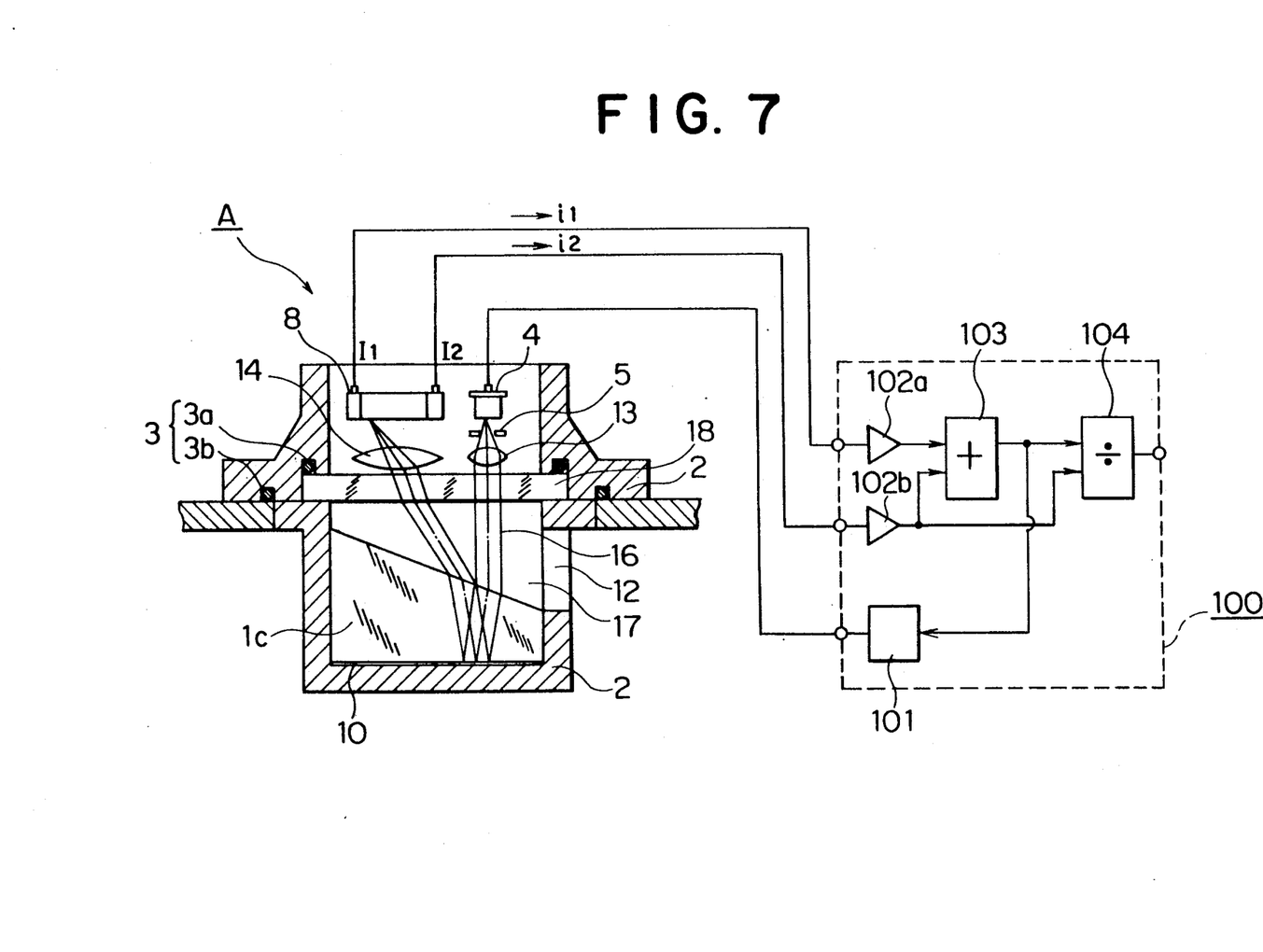
FIG. 7 is a schematic sectional view illustrating a further embodiment of the present invention.

FIG. 7 illustrates further modification of the alcohol concentration detecting apparatus of the present invention. Comparing the structure illustrated in FIG. 7 with that of the embodiments illustrated in FIGS. 1 to 5, it is apparent that the position of the cylindrical transparent body 1c providing the refraction surface 9 is different and that a transparent partition 18 is sealingly mounted between the transparent body 1c and the lenses 13 and 14 to define a substantially wedge-shaped cavity 17 for accommodating the fuel therein between the transparent body 1 and the transparent partition 18. The light emitted from the light-emitting element 4 passes through a light path extending through the diaphragm 5, the collimator lens 13, the transparent partition 18, the cavity 17 filled with the fuel, the refraction surface 9 and the transparent body 1c to reach the reflection mirror 10. The light impinged on the mirror 10 is reflected to return and proceed along a return light path extending through the transparent body 1c, the refraction surface 9, the fuel-filled cavity 17, the transparent partition 18 and the condenser lens 14 to be focused on the light sensing surface of the semiconductor optical position detector 8.

The condenser lens 14 is selected so that the parallel light beam 16 is focused on the optical position detector 8. It is desirable that the light-emitting element 4 is selected to emit a radiation of about 900 nm in order to match the light receiving frequency sensitive region and that the light is provided in the form of pulses so that a dark current dependent upon the temperature of the semiconductor position detector 8 may be eliminated. Also, it is preferable that the transparent partition 18 has a smaller refractive index than the transparent body 1c because the refraction angle at the surface of the transparent partition 18 contacting the atmosphere can be made smaller to decrease reflection and improve the optical efficiency of the optical system, and because the refraction angle at the interface between the fuel in the cavity 17 and the transparent body 1c can be made large so that a large gain of the light impinging position displacement on the optical position detector 8 can be obtained.

Figure 8:
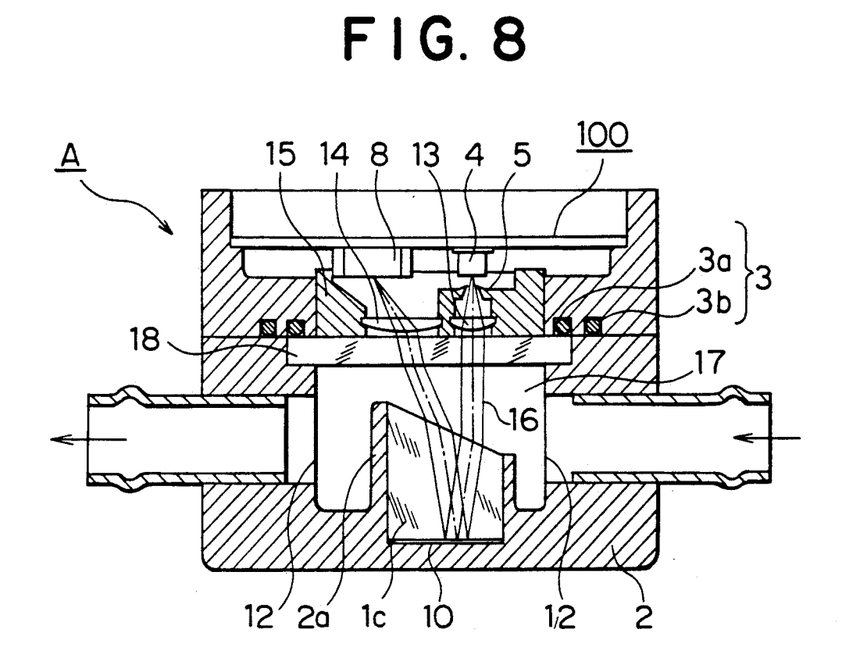
FIG. 8 is a schematic sectional view illustrating another embodiment of the alcohol concentration detecting apparatus of the present invention.

FIG. 8 illustrates another embodiment of the alcohol concentration detecting apparatus of the present invention, in which the transparent body 1c is secured by a suitable bonding agent to a bottom structure or a flange 2a of the casing 2 so that the reflective mirror 10 on the side remote from the refraction surface 9 is not brought into contact with the fuel. Therefore, the reflective mirror 10 is free from the pollution or erosion by the fuel which causes a decrease in the optical efficiency.

Figure 9:
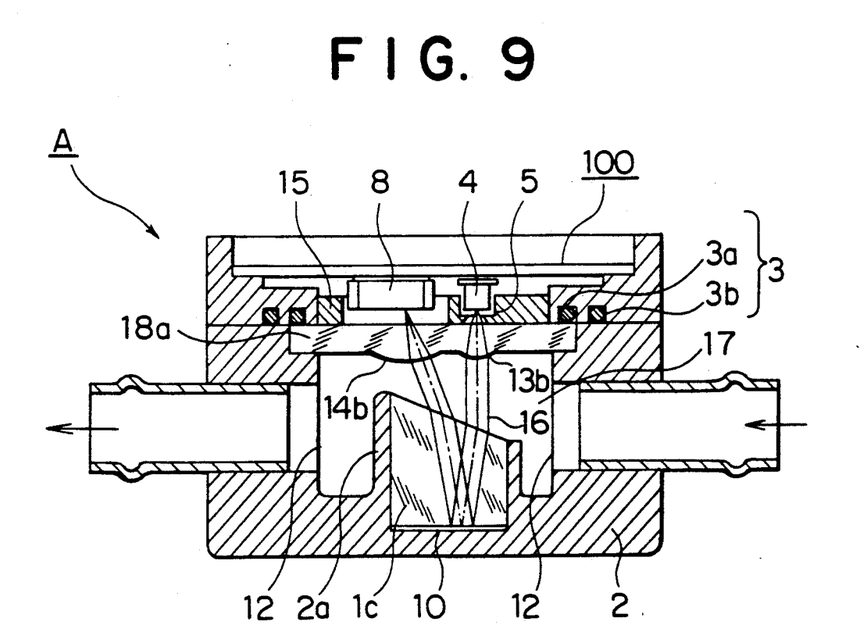
FIG. 9 is a schematic sectional view illustrating a further embodiment of the present invention.

FIG. 9 illustrates another embodiment in which the detector comprises a transparent partition 18a which has integrally formed thereon a collimator lens 13b and a condenser lens 14b. It is seen that the diaphragm 5 is formed as an integral part of the holder 15. This structure is simple and inexpensive.

Figure 10:
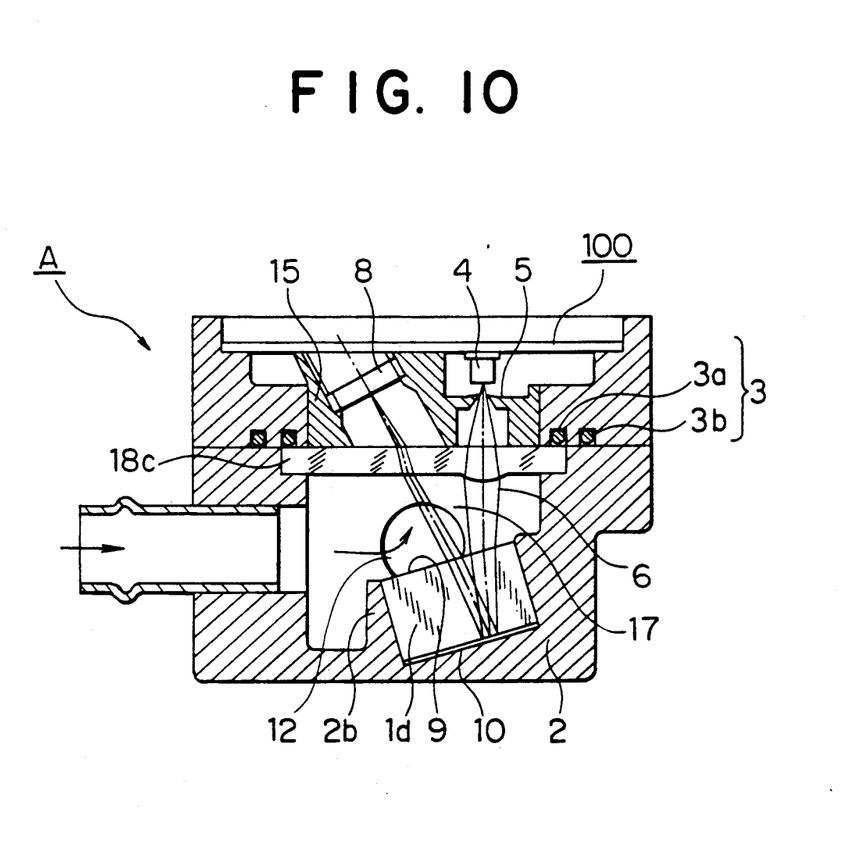
FIG. 10 is a schematic sectional view illustrating another embodiment of the alcohol concentration detecting apparatus of the present invention.

FIG. 10 illustrates a further embodiment of the alcohol concentration detector of the present invention in which the detector comprises a transparent body 1d having the refraction surface 9 and the reflective mirror 10 that are parallel to each other. It is seen that the refraction surface 9 is tilted relative to the light beam 6 so that the substantially wedge-shaped cavity 17 is defined between the refraction surface 9 and the transparent partition 18c. Such the transparent body 1d can be manufactured at a reduced cost, rendering the entire optical system simple and inexpensive. The circumferential surface of the transparent body 1d surrounded by the casing wall 2b may be sealed against the ingress of the fuel by a sealant or a bonding agent filled between the casing wall 2b and the transparent body 1d. Alternatively, the circumferential surface of the transparent body 1d may be metallized and welded or brazed to the casing wall 2b.

As has been described, the alcohol concentration detecting apparatus of the present invention comprises a transparent body having a refraction surface disposed, when in use, in contact with liquid fuel to define a refraction interface between the transparent body and the fuel, the transparent body defining a light path for allowing the light to pass through the refraction surface for refracting the light. A light-emitting element is disposed on one end of the light path and emits a light beam along the light path, and a position detector element disposed at the other end of the light path receives a refracted light beam refracted at the refraction surface and generates an output indicative of the amount of alcohol contained in the fuel. The sensor may comprise a collimator lens disposed in the light path between the light-emitting element and the refraction surface for converting the diverging light emitted from the light-emitting element into a substantially parallel light beam, and a condenser lens disposed in the light path between the refraction surface and the position detector element for focusing the parallel light beam on the position detector element.

Therefore, even when the temperature of the alcohol concentration detecting apparatus changes due to the engine heat and the heated fuel, for example, the output of the detecting apparatus does not vary, so that the detection of the alcohol concentration of the fuel can be precise. Also, the transparent body 1 can be made small, so that the entire alcohol concentration detecting apparatus can be made compact. Further, it is possible to immediately, without delay, detect the alcohol concentration of the fuel that is to be injected from the fuel injection valve at the time of starting of the engine. When the collimator lens and the condenser lens are used, the linearity of the output of the optical position detector is improved.

What is claimed is:

1. An alcohol concentration detecting apparatus, comprising:
    a transparent body (1c,1d) transparent to light and having a refraction surface (9) disposed, when in use, in contact with liquid fuel to define a refraction interface between said transparent body and the fuel, said transparent body defining a light path for allowing said light to pass through said refraction surface for refracting said light;
    a light-emitting element (4) disposed at one end of said light path and emitting a light beam along said light path;
    an optical position detector element (8) disposed at the other end of said light path for receiving a refracted light beam refracted at said refraction surface and generating an output (i1,i2) indicative of the amount of alcohol contained in said fuel;
    an optical lens (13, 13b, 14, 14b) disposed in said light path between said light-emitting element and said light-receiving optical position detector element for directing and focusing a light beam emitted from said light-emitting element onto said optical position detector element; and
    a transparent partition (18, 18a, 18c) disposed between said transparent body and said light-emitting element and between said transparent body and said optical position detector element, said transparent partition defining a substantially wedge-shaped fuel cavity (17) for receiving the fuel therein between said transparent partition and said refraction surface of said transparent body.

2. An alcohol concentration detecting apparatus as claimed in claim 1, wherein said light-path includes a reflective mirror (10) disposed on a side of said transparent body remote from said refractive surface.

3. An alcohol concentration detecting apparatus as claimed in claim 1, further comprising a housing supporting said transparent body therein with said refraction surface in contact with said fuel, said housing having a reflection mirror (10) thereon.

4. An alcohol concentration detecting apparatus as claimed in claim 1, wherein said optical lens comprises a collimator lens (13, 13b) for converting said light beam from said light-emitting element into a substantially parallel beam (16), and a condenser lens (14, 14b) disposed in said light path between said fuel cavity and said optical position detector.

5. An alcohol concentration detecting apparatus as claimed in claim 4, wherein said collimator lens (13) and said condenser lens (14) are elements separate from said transparent partition (18).

6. An alcohol concentration detecting apparatus as claimed in claim 4, wherein said collimator lens (13b) and said condenser lens (14b) are integral with said transparent partition (18a).

7. An alcohol concentration detecting apparatus as claimed in claim 1, wherein said position detector element comprises a semiconductor position detector element.

* * * * *